United States Patent [19]
Bone et al.

[11] Patent Number: 5,936,724
[45] Date of Patent: Aug. 10, 1999

[54] FLICKER PHOTOMETER

[75] Inventors: Richard Andrew Bone; John Thomas Landrum; Wenlue Huang, all of Miami; Carlos Manuel Orta, Homestead, all of Fla.

[73] Assignee: The Howard Foundation, United Kingdom

[21] Appl. No.: 09/038,420

[22] Filed: Mar. 11, 1998

[30] Foreign Application Priority Data

Mar. 11, 1997 [GB] United Kingdom ............ 9704972

[51] Int. Cl.[6] ................ G01J 1/34; G01J 1/36; G01J 1/00; G01J 1/60
[52] U.S. Cl. .................. 356/217; 356/213; 356/214
[58] Field of Search .................. 356/213, 214, 356/217, 418, 419

[56] References Cited

U.S. PATENT DOCUMENTS

| | | | |
|---|---|---|---|
| 2,471,249 | 5/1949 | Stearns | 88/14 |
| 3,787,124 | 1/1974 | Lowy et al. | 356/188 |
| 3,811,781 | 5/1974 | Lowy | 356/188 |
| 3,819,256 | 6/1974 | Bellows et al. | 356/126 |
| 4,515,165 | 5/1985 | Carroll | 128/664 |

FOREIGN PATENT DOCUMENTS

| | | |
|---|---|---|
| 1161440 | 8/1969 | United Kingdom . |
| 1 221 066 | 2/1971 | United Kingdom . |
| 2 301 775 | 12/1996 | United Kingdom . |

Primary Examiner—Frank G. Font
Assistant Examiner—Roy M. Punnoose
Attorney, Agent, or Firm—Lee, Mann, Smith, McWilliams, Sweeney & Ohlson

[57] ABSTRACT

A flicker photometer has beam generating means (1, 8 and 4) for generating two beams of light of different colors. Light from the beams is viewed at the viewing means, and the intensity of light of one beam relative to that of the other beam can be adjusted by adjustment means comprising an attenuating filter (20) which is movably mounted in the path of one beam. Movement of the filter relative to the beam alters the degree to which the beam is attenuated, and is achieved using an electric motor (22). The motor provides a relatively easy means of adjusting the filter position, and can be used to provide coarse and fine adjustments in response to suitable signals from an optical encoder. The motor also enables the filter, along with the beam generating means, to be mounted on a movable table for use in enabling the photometer to accommodate both short and long-sighted subjects.

14 Claims, 14 Drawing Sheets

FLICKER PHOTOMETER

FIELD OF THE INVENTION

This invention relates to a flicker photometer, and more particularly to a flicker photometer for measuring the optical density of macular pigment in the human eye.

BACKGROUND TO THE INVENTION

Macular pigment is the yellow pigment situated in the central portion of the human retina. The absorption spectrum for the pigment has a peak for light of a wavelength of 460 nm, and zero for light of a wavelength of 540 nm, so that the pigment absorbs significant amounts of the shorter wavelength light, whilst having little or no effect on light of the longer wavelength.

The highest concentrations of macular pigments are to be found in the region of the retina which has a very high number density of cone receptors, and is coupled to a disproportionately large area of the visual cortex, giving that region a high degree of visual acuity.

It has been proposed that the macular pigment protects the retina against harmful effects of short wavelength radiation, and accordingly much effort has been devoted to measuring the optical density of macular pigment in various subjects in order to determine whether there is any correlation between irregularities in the amount of macular pigment present in various subjects and certain sight defects.

To that end, a flicker photometer projects green and blue light (respectively of wavelengths of 540 nm and 460 nm) into a subject's eye in an alternating sequence. The subject is able to vary the intensity of light of one of those wavelengths until, if the frequency of alternation is sufficiently high, the subject perceives a minimum or no flickering of light projected into his or her eye. When this condition is achieved, the relative intensities of light of the different colours are calculated and that calculation is used to provide an indication of the optical density of macular pigment.

One example of such a photometer is described in the article "Comparison of Macular Pigment Densities in Human Eyes" (R A Bone and J M B Sparrock: Vision Res. Vol. 11, pp 1057–1064. Pergamon Press 1971).

In that photometer, a subject could vary the intensity of light from one or two beams by altering the position of a wedge-shaped filter. The position of the filter relative to the beam is related to the depth of filter through which the beam travels, and hence the degree of attenuation of the beam.

However, movement of the filter is achieved using a mechanical linkage. However, such a linkage can be cumbersome, and does not facilitate fine adjustments of the wedge position over the necessary range of wedge movements.

SUMMARY OF THE INVENTION

According to the invention, there is provided a flicker photometer comprising beam generating means for generating two beams of light of different wavelengths, viewing means for enabling a subject to view light from the beams incident on the viewing means, shutter means for causing the incidence of light from one beam on the viewing beam rapidly to alternate with that of light from the other beam, and adjustment means for adjusting the intensity of light from one beam relative to that of the other beam, wherein the adjustment means comprises an attenuating filter movably mounted in the path of one beam, the filter being so arranged that movement of the filter relative to the beam alters the degree to which the filter attenuates the beam, and an electric motor for moving the filter relative to the beam to achieve said adjustment.

The electric motor provides a particularly convenient and effective way of adjusting the position of the filter, so that the motor can readily be controlled, by means of external electrical controls, by the subject, and no mechanical linkage is needed between the controls and the filter.

Preferably, the motor is a stepper motor, and preferably the motor operates in response to pulsed signals derived from control means mounted on the exterior of the photometer.

Preferably, the control means comprises a dual-phase optical encoder for generating two sets of pulses, the frequency of which represents the degree of movement of the encoder, and the relative phase of which represents the direction in which the encoder has been moved, and hence the direction in which the filter is to move, the optical encoder being connected to control means for causing the motor to rotate in the required direction and by the required angle in response to said signals from the encoder.

Preferably, the control means can selectively provide coarse and fine control of the movement of the motor, for any given movement of the optical encoder.

Thus, a subject can use the coarse control, relatively rapidly to move the filter to a position close to that corresponding to minimum or no flicker, and can then use the fine adjustment facility, more precisely to move the filter into that position.

Conveniently, the optical encoder comprises a rotary knob.

Preferably, the filter comprises a graded filter. For example, the filter may comprise a wedge, so mounted for linear movement relative to the beam that said movement varies the thickness of the portion of the wedge through which the beam passes, and hence the degree of attenuation of the beam.

Preferably, the photometer includes screen means for scattering light from the beams before that light enters the viewing means.

In this case, the beam generating means, adjustment means, shutter means and screen means are preferably mounted on a table which is movable relative to the viewing means to enable the photometer to accommodate both near and far-sighted subjects.

This enables the subject, in effect, to focus the photometer without actually moving the viewing means, and this helps to ensure that the subject's head is properly positioned. The movement between the motors and the controls which control its operation can readily be accommodated by, for example, the inherent flexibility of wires connecting the motor to the controls.

The invention also lies in a flicker photometer comprising beam generating means for generating two beams of light of different wavelengths, viewing means for enabling a subject to view the light from the beams incident on the viewing means, shutter means for causing the incidence of light from one beam on the viewing means rapidly to alternate with that of the other beam, adjustment means for adjusting the intensity of the light from one beam to that of the other beam, wherein the generating means, adjustment means and shutter means are mounted on a table which is movable relative to the viewing means to enable near and far-sighted subjects to use the photometer.

BRIEF DESCRIPTION OF THE DRAWINGS

The invention will now be described, by way of example only, with reference to the accompanying drawings, in which.

DETAILED DESCRIPTION

Figure 1:
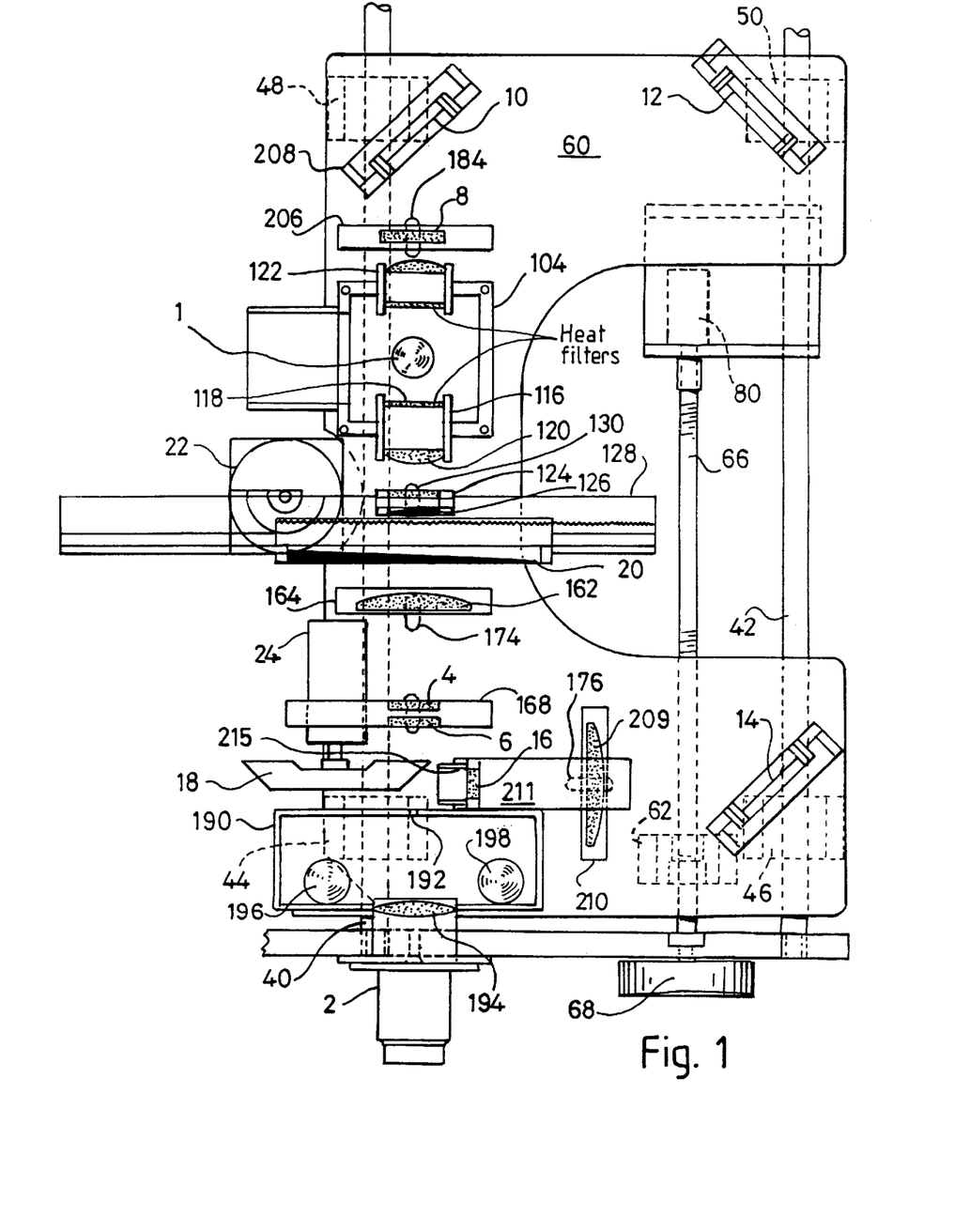
FIG. 1 is a diagrammatic plan view of various components of a flicker photometer in accordance with the invention.
Figure 2:
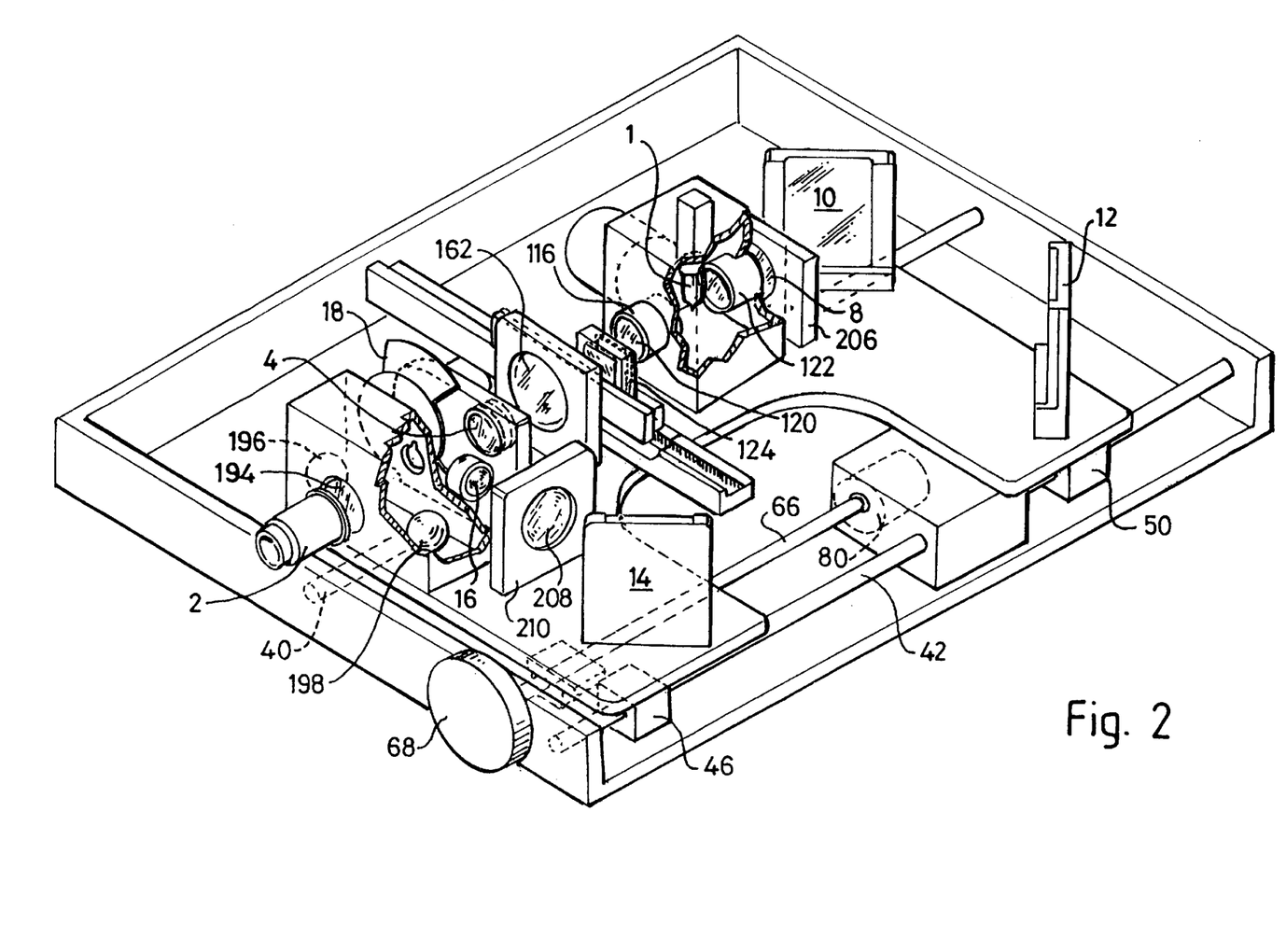
FIG. 2 is a partially cut away isometric view of those components.

With reference to FIGS. 1 and 2, a photometer in accordance with the invention uses a single light source in the form of a 150 W quartz halogen lamp 1 to generate two beams of light, one of which travels directly towards viewing means, which comprises an eye-piece 2, via a 460 nm interference filter 4 and ground glass diffusing screen 6. The other beam travels through a 540 nm interference filter 8, and is reflected by angled mirrors 10, 12 and 14 along a path which coincides with a second ground glass diffusing screen 16 and a rotary shutter 18. The rotary shutter is driven by a motor 24, and allows light from either one of the beams to enter the eye-piece, whilst blocking the light from the other beam. Which light is blocked, and which reaches the eye-piece 2, will depend upon the angular position of the shutter 18 so that rotation of the latter causes the incidence of light from the beams on the eye-piece 2, and hence the colour of light reaching the eye-piece, to alternate at a frequency related to the speed of rotation of the shutter 18.

Before reaching the shutter 18, the first of the above-mentioned beams is passed through a graded, neutral density wedge filter 20 which is movable under the control of a stepper motor 22 so as to vary the extent of attenuation of the first beam by the filter 20.

Figure 3:
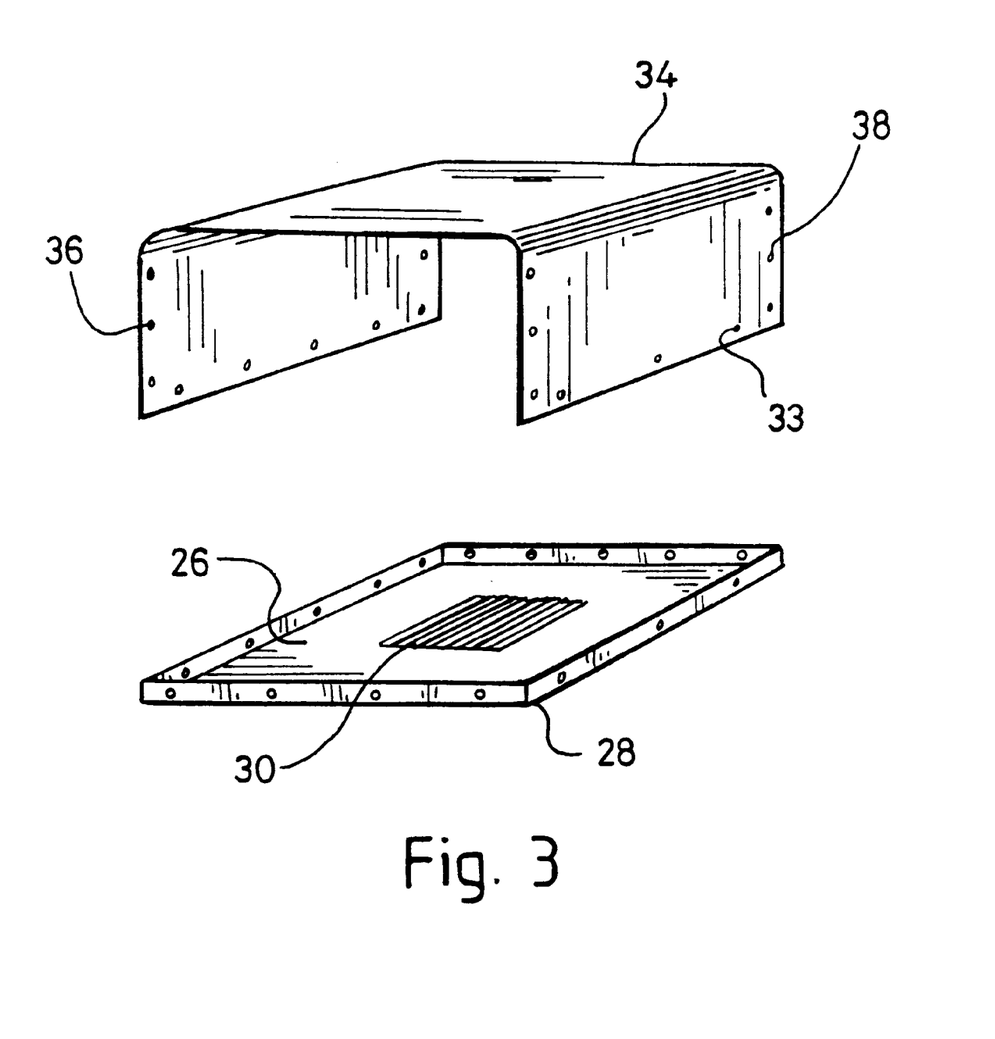
FIG. 3 is an isometric view of a housing for the components shown in FIGS. 1 and 2.

The components of the photometer are contained within the housing shown (in exploded form) in FIG. 3. The housing comprises a rectangular tray 26 having an upstanding peripheral wall 28 and a central ventilation grid 30. The peripheral wall 28 has holes which enable the base 28 to be bolted to an inverted u-shaped cowell 34 having corresponding holes, for example 33, for receiving the bolts.

The cowell 34 includes further holes, such as 36 and 38 which enable the attachment of front and rear face plates (not shown). The eye-piece 2 is directly attached to the front of the face plate, on which a number of other controls (described below) are also mounted.

Referring back to FIGS. 1 and 2, a pair of cylindrical rails 40 and 42 are mounted on the tray 26, and four bearing blocks 44, 46, 48 and 50 are slidably mounted on the rails 40 and 42. The bearing block 46 is shown in more detail in FIGS. 5 and 6. The other bearing blocks are identical to the block 46.

Figures 4, 4A:
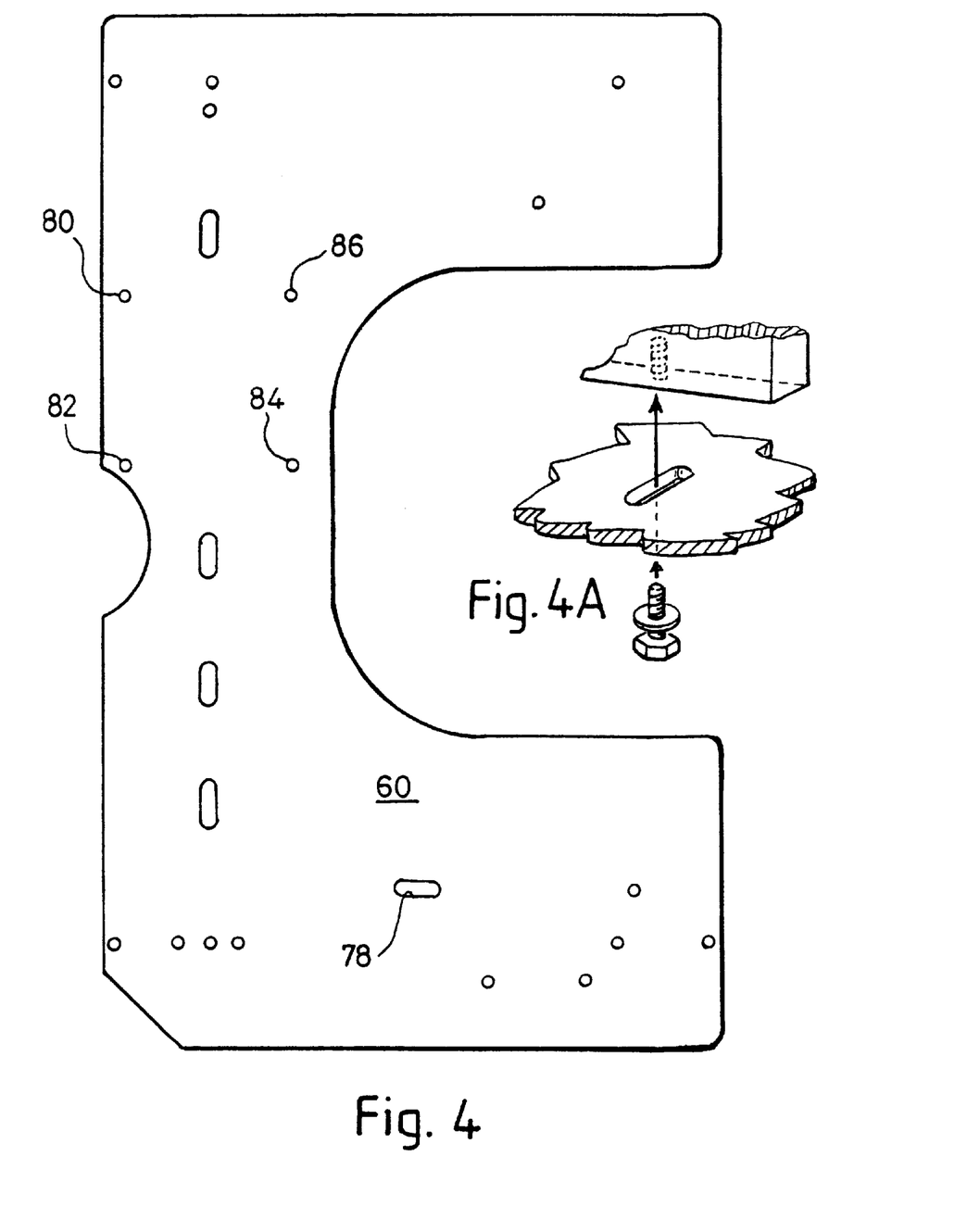
FIG. 4 is a plan view of a table, which is one of the components shown in FIGS. 1 and 2, and on which various components of the photometer are mounted.
FIG. 4A shows how one of the components is attached to the table.
Figure 5:
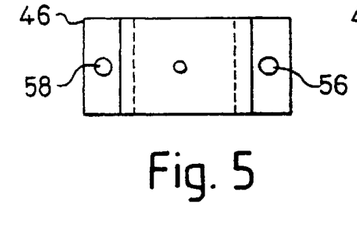
FIGS. 5 and 6 are views respectively of the underside and front of a bearing block through which the table is mounted on rails.
Figure 6:
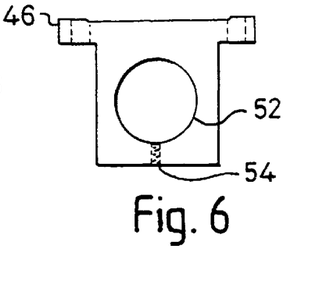

Block 46 includes a central cylindrical passage 52 which is lined with a ball bushing linear bearing assembly (not shown) held in position by means of a grub screw 54 which is accommodated in a screw-threaded passage in the bottom of the block 46. The linear bearings enable the block 46 to slide freely along the rail 42. The top of the bearing block 46 includes a pair of overhangs which project from opposite sides of the block 46, and which include through bores 56 and 58 which enable the block 46 to be attached to a table 60 (FIG. 4) by bolts passing through the through bores 56 and 58 and corresponding through bores in the table 60.

The blocks 44, 48 and 50 are attached to the table 60 in a similar fashion, so that the table 60, and the components which it carries, can move in either direction along the rails 40 and 42.

Figure 7:
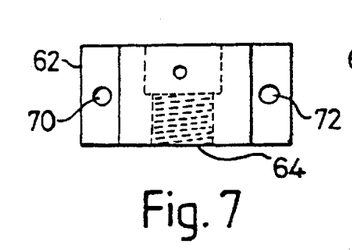
FIGS. 7 and 8 are respective plan and front views of part of a drive mechanism for the table.
Figure 8:
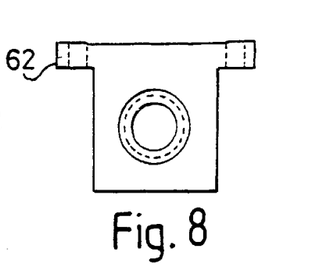

A further block 62 is bolted to the underside of the table 60, and is shown in more detail in FIGS. 7 and 8. The block 62 includes a screw-threaded passage 64 through which a screw-threaded worm shaft 66 extends. The shaft 66 is rotatably mounted on the base 26 in a fixed axial position, and is terminated at one end in a crank handle 68. The shaft 66 also extends through the front plate of the photometer housing so that a subject can operate the handle 68, and thereby move the table 60 in either direction along the rails 40 and 42. This movement of the table does not cause any movement of the eye-piece 2 since the latter is attached to the front plate of the housing, and the movement of the table enables the image seen through the eye-piece 2 to be focused.

The end of the shaft 66 opposite the handle 68 is connected to a motor 80 mounted on the tray 26. The motor 80 can be operated by buttons (not shown) on the front plate to provide power assisted focusing of the image seen through the eye-piece 2.

The block 62, like the block 46, has overhangs which accommodate through bores 70 and 72 for enabling the block 62 to be bolted to the underside of the table 60.

With reference to FIGS. 4, and 4A, table 60 also includes a number of slots, for example 78, for enabling components to be attached to the table by means of a screw-threaded bolt which extends from the underside of the table 60, through the slot, and into a screw-threaded blind bore in the base of a holder for the component. The slots allow the positions of the corresponding holders to be adjusted since each bolt can extend through its slot at any position along the length of the latter. Thus adjustments of the position of a holder can be made by loosening or removing the bolt, re-positioning the holder (whilst ensuring that its blind bore still wholly overlies the slot) and then screwing the holder onto the table in its new position thereon.

Some of the components, for example the mirrors 10, 12 and 14, remain in the same position on the table 60, however the photometer is set up, and these are fastened to the table 60 by bolts which pass through circular holes in the table 60 into screw-threaded blind bores in the bases of the holders of those components. For example, the table 60 has four holes 80, 82, 84 and 86 through which a housing 104 for the lamp 1 is attached in a fixed position on the table 60.

Figures 9, 10:
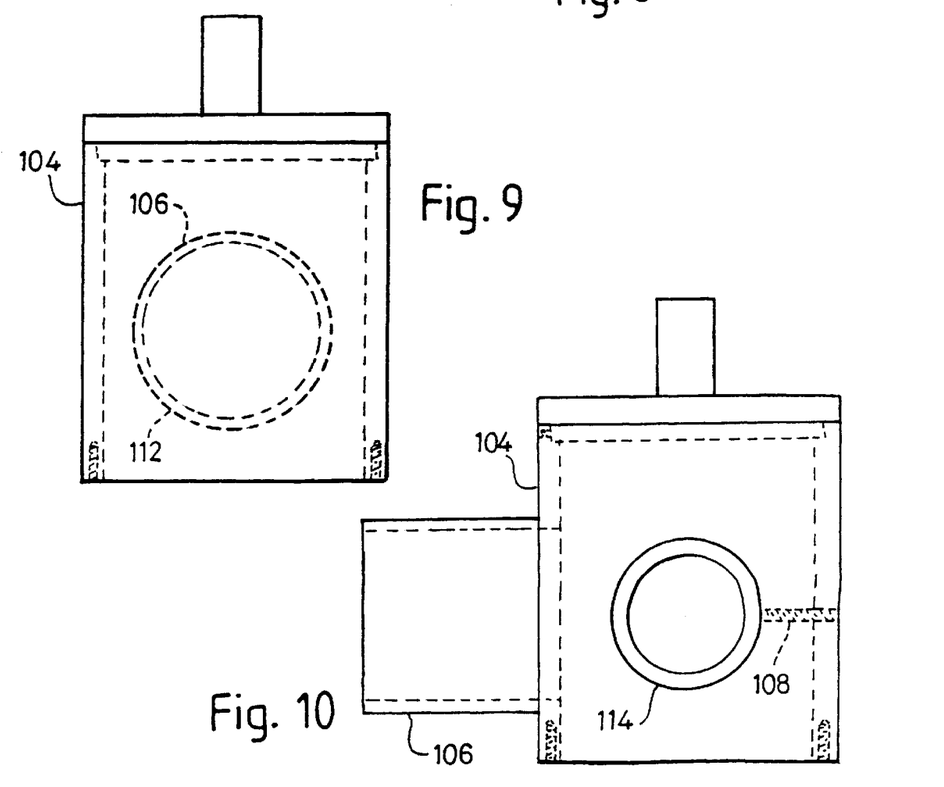
FIGS. 9 and 10 are respective side and front views of a lamp housing mounted on the table.

The housing 104 is generally rectangular in plan, and is shown in detail in FIGS. 9 and 10. The left side of the housing 104 (as viewed in FIG. 10) includes a cooling port 112 which is connected to an air duct 106 connected in turn to a fan (not shown) and an outlet port (not shown) in the cowell 34. The fan draws air over the lamp 1 to cool the latter.

A further aperture 114 is provided in the front face of the housing 104, and accommodates a cylindrical housing 116 for an infrared filter 118 and a collimating lens 120 situated downstream of the filter 118. A similar lens and filter arrangement are accommodated in a further housing 122 situated in an aperture in the rear face of the housing 104. The housings 116 and 122 are held in position on the housing 104 by means of grub screws extending respectively through screw-threaded passages (for example 108) in the front and rear faces of the housing 104.

Figures 11, 12A:
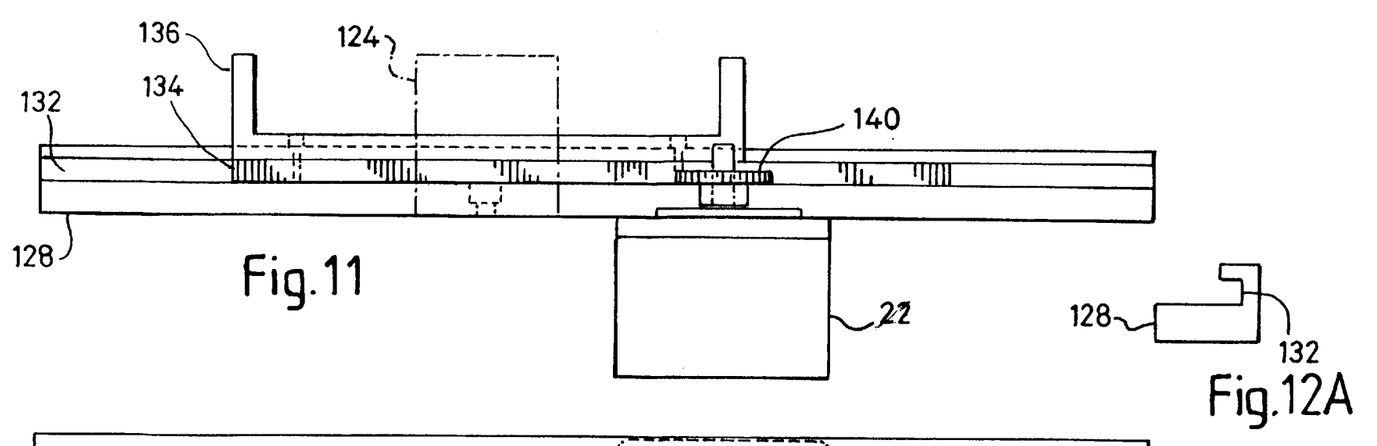
FIGS. 11 and 12 show certain components of adjustment means which are mounted on the table, the adjustment means being shown from the rear in FIG. 11 and in plan in FIG. 12.
FIG. 12A is an end view of part of the adjustment means.
Figure 12:
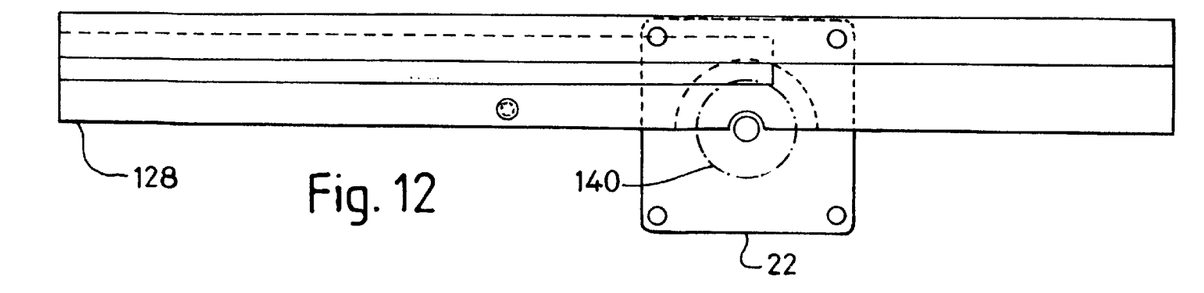

The lens 120 forms a beam of light which is directed on to a compensator 124 comprising a wedge filter member 126 which tapers in the opposite direction from the wedge 20. The wedge filter member 126 compensates for the lateral variation in the attenuation of the beam by the filter 20. The compensator 124 is mounted on a shelf 128 which is shown in end view in FIG. 12A, and which is screwed on to the table 60 at slot 130. The shelf 128 is formed with a track 132 running along its length. The track 132 accommodates a rack 134 which is slidable along the track 132 and forms part of a mounting bracket 136 for the wedge filter 20. The bracket 136, and hence the filter 20, is moved along the shelf 128 by means of a pinion wheel 140 which engages the rack 134, and is driven by the stepper motor 22 which is suspended from the underside of the shelf 128. For the sake of clarity, the wedge filter 20 has been omitted from FIGS. 11 and 12.

The angular position of the output shaft of the stepper motor is monitored by a position sensing potentiometer 142 (FIG. 13), the output of which therefore gives an indication of the position of the neutral density wedge filter 20, and hence the extent of attenuation of the light beam passing through the filter 20.

Figure 13:
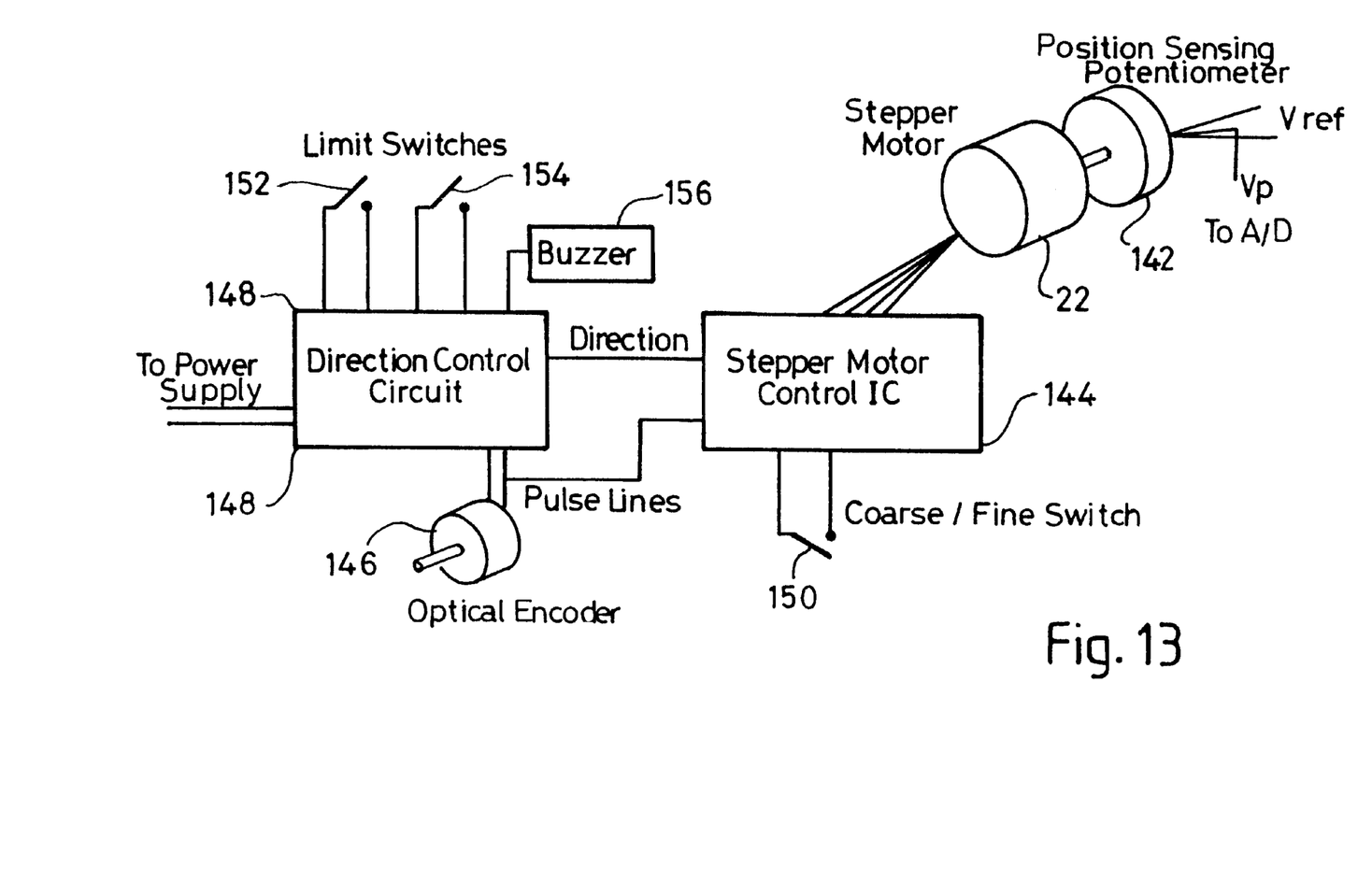
FIG. 13 is a block diagram showing a control system for the adjustment means.

The stepper motor 22 is controlled by a stepper motor control integrated circuit 144, which is in turn connected to a dual phase optical encoder 146 and a direction control circuit 148. The encoder 146 is connected to a rotary knob (not shown) accessible from outside the housing, and is operable to send a train of pulses to the stepper motor control integrated circuit 144 to control the speed of rotation of the motor, and to send two trains of pulses to the direction control circuit 148, which determines the phase difference between the two trains of pulses.

That phase difference is dependent upon the direction of rotation of the rotary knob, and therefore provides an indication of the direction in which the motor 22 is to be driven. The direction control circuit accordingly then supplies a suitable direction signal to the circuit 144.

Thus, the motion of the stepper motor 22 corresponds to the motion of the rotary knob.

In addition, the circuit 144 is connected to a coarse/fine switch 150 which can be used to send a signal to the circuit 144 to change the drive pulse sequence to the motor 22 to provide full-step or half-step motor rotation in response to rotation of the rotary knob, and thus providing coarse or fine control of the position of the wedge filter 20.

Furthermore, two limit switches 152 and 154 are connected to the control circuit 148 as is a buzzer. The switches are located at either end of the track 132, and each switch can be closed by contact with the rack 134. When the rack 134 reaches either of the switches, the direction control circuit 148 immediately reverses the direction of rotation of the motor 22, whilst a buzzer 156 (connected to the control circuit 148) emits an audible warning signal.

Referring back to the potentiometer 142, a fixed reference voltage $V_{REF}$ is placed across the potentiometer 142 such that the wiper voltage $V_P$ indicates the angular position of the potentiometer 142, and hence the wedge position. An analogue to digital conversion circuit (158 in FIG. 25) which in turn converts the analogue voltage $V_P$ into digital form and feeds the digital signal into a single chip microcomputer 160 (FIG. 26) which acts as a data processing device and an interface for an external printer 218 (FIG. 26).

Figure 14:
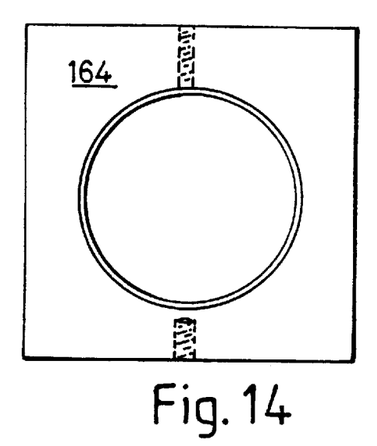
FIGS. 14 and 15 are respective front and side views of a lens mounting block for the photometer.
Figure 15:
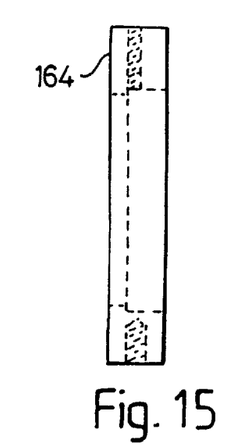

The portion of the beam which is transmitted through the filter 20 also passes through a plano-convex condenser lens 162 which is located in a mounting block 164 shown in more detail in FIGS. 14 and 15. The mounting block 164 is screwed on to the table 60 using a slot in the latter which allows some adjustment of the position of the holder.

Figure 16:
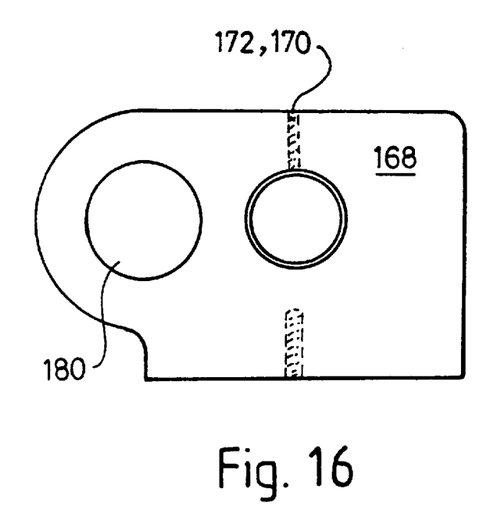
FIGS. 16 and 17 are respective front and side views of a mounting block for a filter, diffusing screen and shutter of the photometer.
Figure 17:
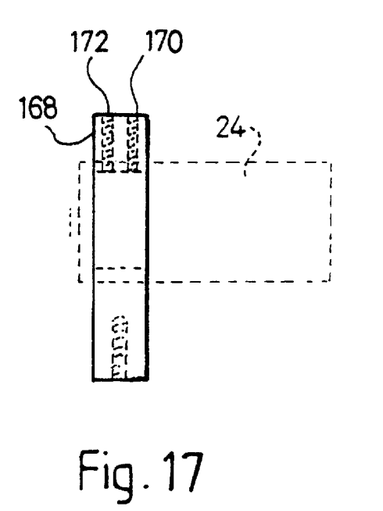

The condenser lens 162, in turn, focuses a beam of light on to the 460 nm interference filter 4 and the translucent diffusing screen 6, both of which are held in a mounting block 168 shown in more detail in FIGS. 16 and 17. The filter 4 and screen 6 are retained in the block 168 by means of grub screws 170 and 172.

The block 168 is screwed onto the table 60 at slot 174, and includes a circular aperture 180 in which the motor 24 is retained by means of a grub screw (not shown).

Figure 18:
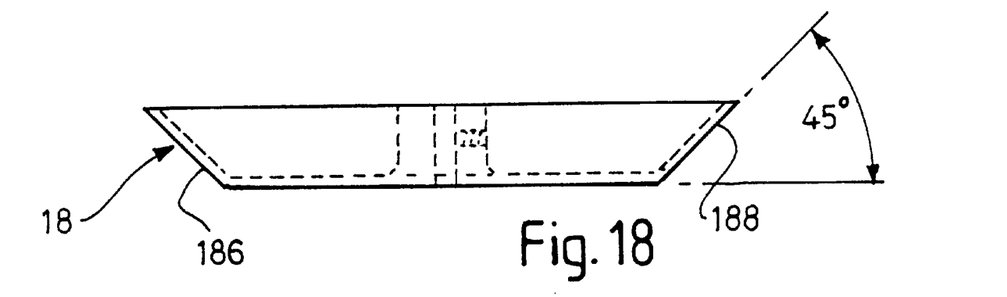
FIGS. 18 and 19 are respective plan and front views of the shutter.
Figure 19:
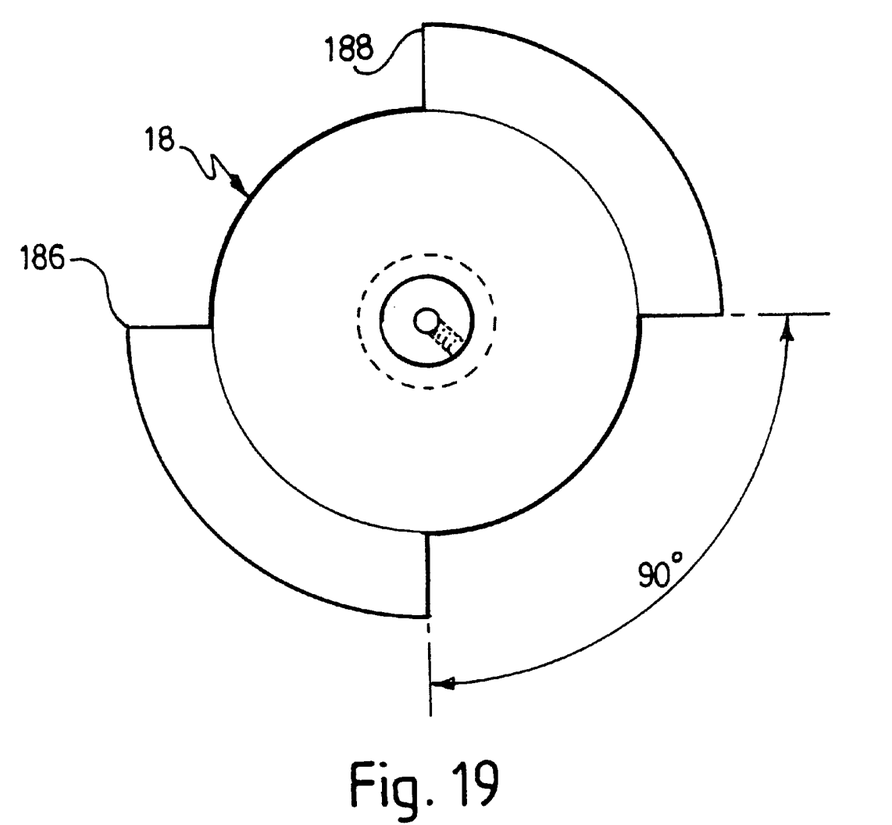

With reference to FIGS. 18 and 19, the shutter 18, which is connected to the output shaft of the motor 24 comprises a disc which incorporates a bevel which is sectored so as to be in two portions 186 and 188. As can be seen from FIG. 18, each bevel portion 186 and 188 extends at an angle of 45° to the plane of the disc 18, which has a matt white surface finish.

Figure 20:
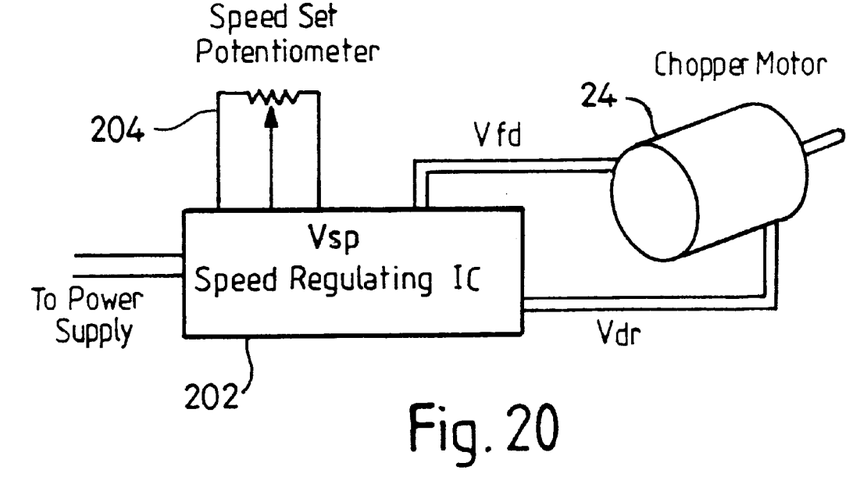
FIG. 20 is a block diagram of the control system for the shutter motor.

The motor 24 is a DC motor which has a built-in tachometer, and the speed of the motor 24 is controlled by a control circuit 202 as shown in FIG. 20, by means of a potentiometer 204, which can be operated by the subject who can thus set the speed of rotation of the shutter 18 in the range of 300 to 2,400 rpm. The potentiometer 204 sets a voltage $V_{sp}$ which determines the speed of the motor 24. The circuit 202 compares $V_{sp}$ with a feedback voltage from the tachometer, $V_{fd}$, and generates a driving voltage $V_{dr}$ to drive and maintain the shutter 18 at the desired speed.

A viewing box 190 is located immediately adjacent the disc 18, and includes an aperture 192 to which light from the beams generated by the lamp 1 is incident on an achromatic magnifying lens 194 of the eye-piece 2. The aperture 192 contains cross-hairs.

The box 190 also contains a pair of incandescent lamps 196 and 198 for illuminating the white background provided by the interior of the box at the same brightness as the aperture 192 (as seen by the subject) in order to maintain the subject's retina at a fixed adaptation level.

The box 190 also contains a light emitting diode 200 (FIG. 28) which a subject can look at if the response of a non-central region of the retina (i.e. a region containing substantially no macular pigment) is to be analysed.

Figure 28:
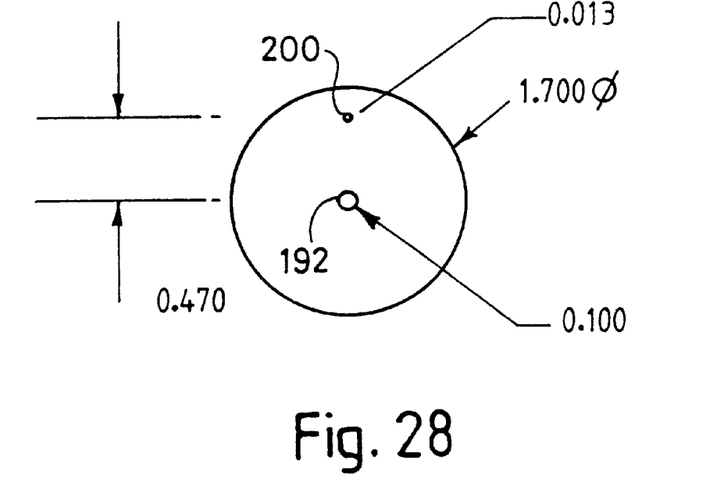
FIG. 28 illustrates the view presented by the photometer to a subject looking through an eye-piece or the photometer.

Thus, in practice, two wedge positions are determined, one while the subject views the aperture 192 centrally, and a second while the subject views the LED 200. The latter measurement determines the inherent relative sensitivity of the subject's retina to 460 and 540 nm light. The central measurement then reveals the additional amount of 460 nm light required to compensate for that which the macular pigment has absorbed. The central macular pigment optical density is given by the difference between the two wedge optical densities obtained with central and peripheral viewing.

Figure 21:
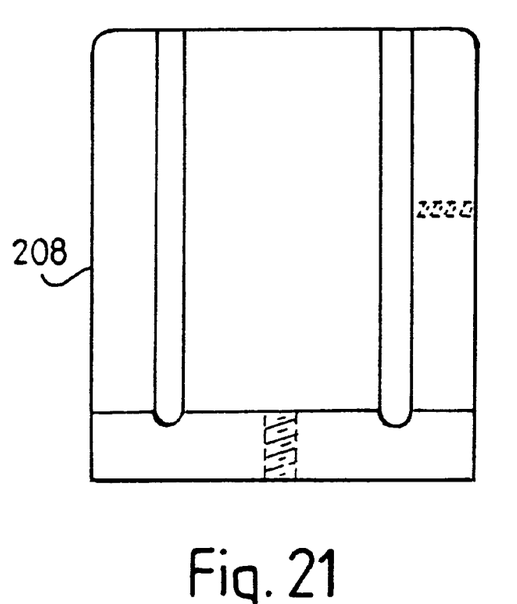
FIGS. 21 and 22 are respective front and side views of an example of mounting block for mirrors used in the photometer.
Figure 22:
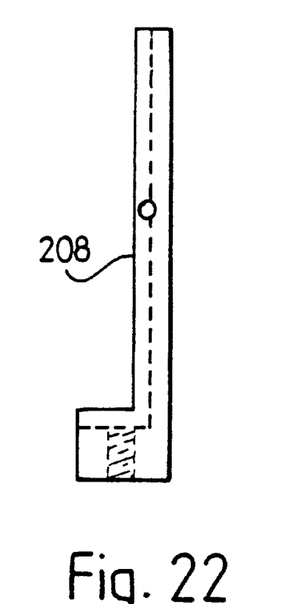

The filter 8 is attached to a mounting block 206, which is in turn attached to the table 60 at slot 184. The mirror 10 is held within a mounting block 208, shown in FIGS. 21 and 22, which is directly screwed on to the table 60 at a fixed position defined by holes in the latter. Similar mounting blocks are provided for the mirrors 12 and 14.

Figure 23:
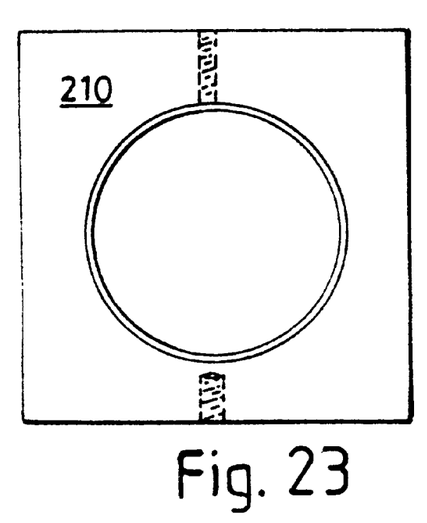
FIGS. 23 and 24 show a further lens mounting block for the photometer.
Figure 24:
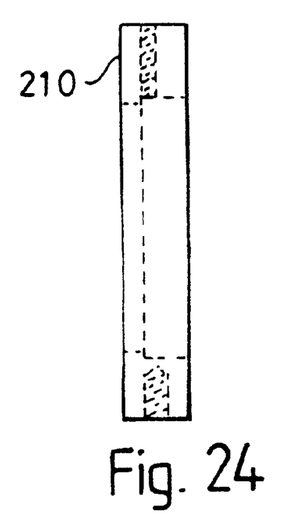

The beam which has passed through the 540 nm interference filter 8 is reflected by the mirrors 10, 12 and 14 and is directed on to a plano-convex condenser lens 209 attached, by a grub screw (not shown), to a mounting block 210 which is shown in more detail in FIGS. 23 and 24, and which is screwed on to the table 60 at slot 176. The holder 210 also carries an arm 211 which is attached to the top of the holder 210 at one end. The other end of the arm 211 includes a holder 215 for the screen 16. For the sake of clarity, the arm 211 has been omitted from FIG. 2. The lens 208 focuses that beam on to the diffusing screen 16 (which is formed from ground glass). If one of the bevelled portions 186 and 188 is in registry with the aperture 192, light transmitted through the screen 16 is scattered and directed from that bevel into the aperture 192. If, on the other hand, one of the spaces between the bevelled portions is in registry with the aperture 192, virtually no light from the screen 16 reaches the aperture 192, and instead light from the screen 6 is allowed to enter the aperture.

Figure 25:
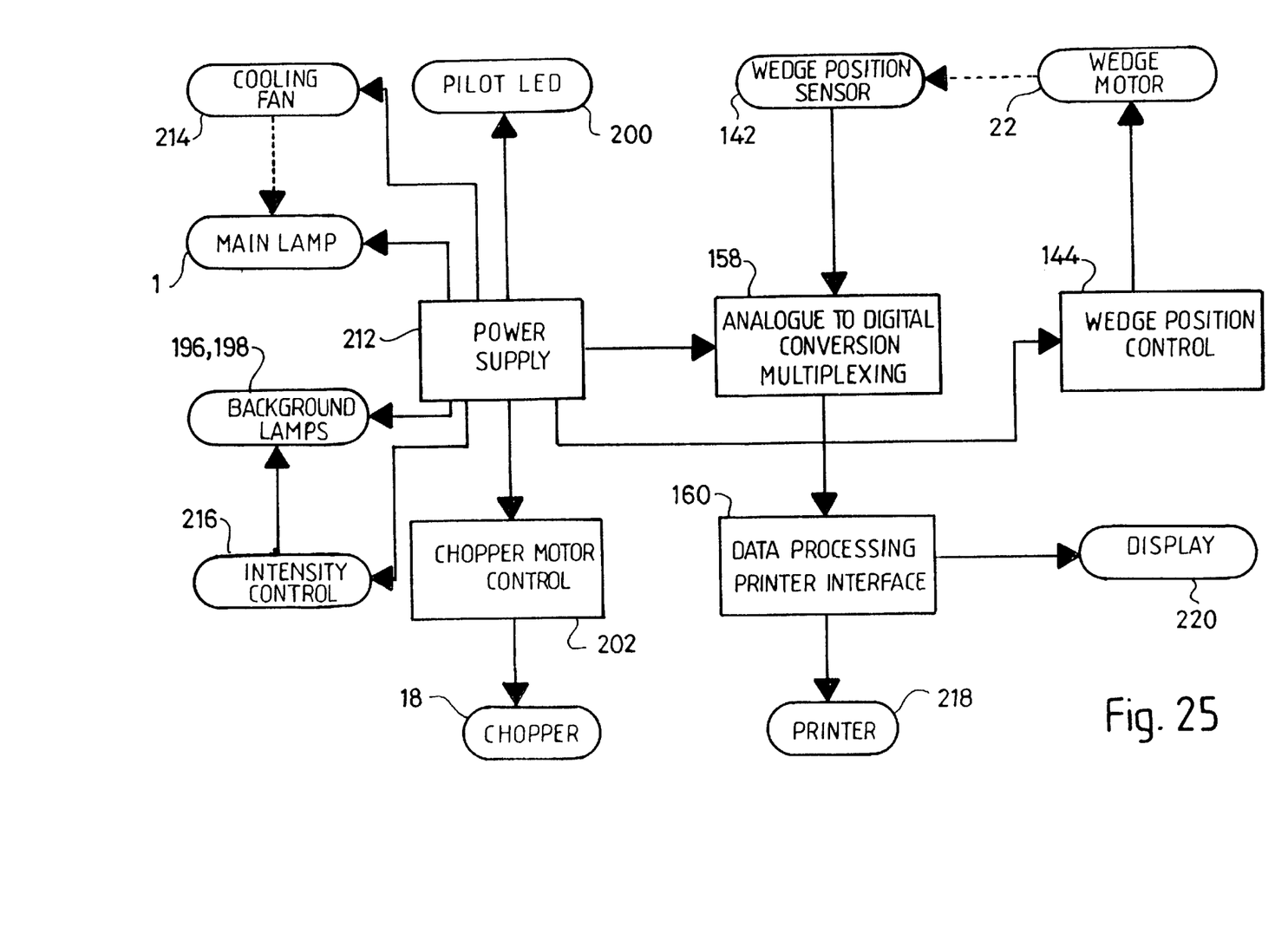
FIG. 25 is a block diagram of various components of the photometer.
Figure 26:
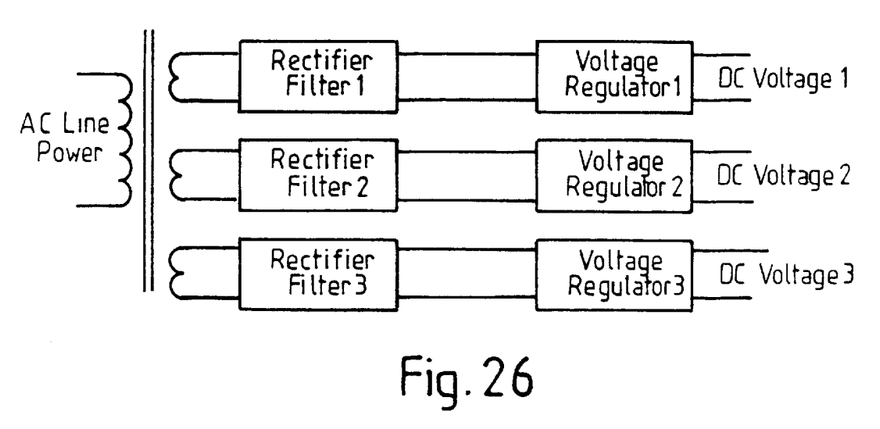
FIG. 26 is a block diagram of a power supply for the photometer.
Figure 27:
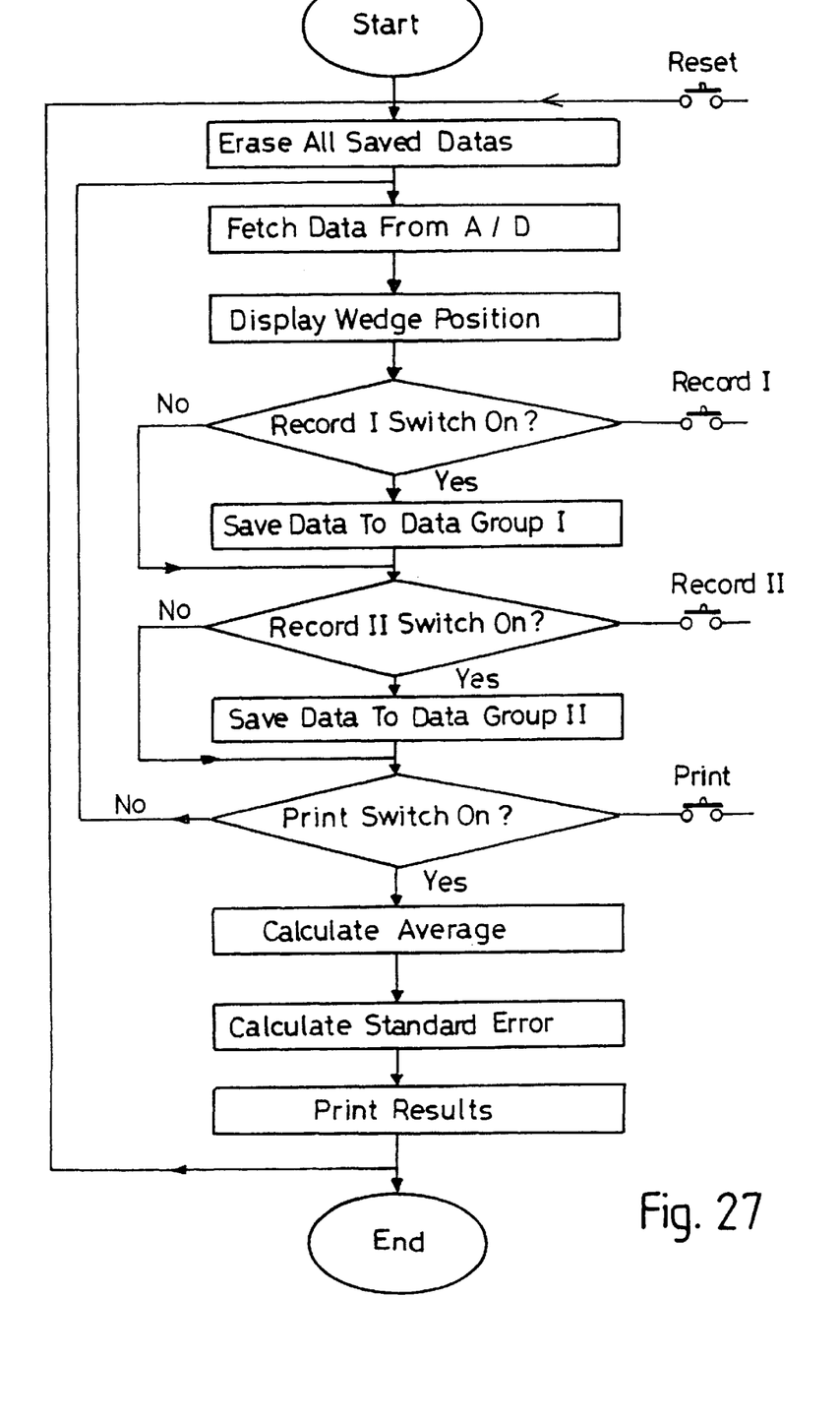
FIG. 27 is a flow chart illustrating the operation of the photometer.

As can be seen from FIG. 25, the electrical power for various components of the photometer is provided by a power supply 212, which supplies power to a cooling fan 214 for the lamp 1 and intensity control circuitry 216 for the bulbs 196 and 198. The photometer also includes a data output port at the data processing printer interface 160, which allows connection to an external printer 218. The interface 160 is also connected to a volatile display, such as an LCD display, 220 mounted on the housing of the photometer. The display provides information on positions of the wedge 20, rotational speed of the shutter 18 and instructions to the user.

With reference to FIG. 26, the power supply 212 is adapted to be connected to the AC mains supply, and incorporates a number of rectifiers and voltage regulators for deriving various DC voltages from the AC input. The following table shows the voltages and currents which are supplied by the power supply 212.

| Voltage | Current | To Element(s) |
| --- | --- | --- |
| 15 VAC | 10 A | Main Lamp |
| 3–15 VDC | 3.5 A | Background Lamp/Intensity Control |
| 24 VDC | 0.5 A | Wedge Motor |
| 12 VDC | 1 A | Cooling Fan, Chopper, Wedge Motor Controller |
| +5 VDC | 2 A | Data Processing A/D, Display, Wedge Control, LED |
| −5 VDC | 0.05 A | A/D |

In addition to the handle 68 the controls for the motor 80, the speed of operation of the motor 24 and the position of the wedge 20, the subject using the photometer has access to a reset button, two record buttons a print button and input buttons for selecting the number of measurements to be made (in response to a prompt provided by the volatile display), all of which are connected to the data processing and printer interface 160.

With reference to FIG. 28, the subject initially adjusts the position of the table 60, and hence all the components carried on it, using the hand wheel or motor 80, until the cross-hairs in the aperture 192 are in focus. The photometer can thus accommodate both near and far-sighted individuals and can be adjusted without altering the position of a user's head relative to the housing. The user then selects a number of measurements to be made and an initial speed for the shutter 18, and then presses a reset button which erases any data saved from previous measurements made by the photometer.

The rotating shutter 18 causes the aperture 192 to be illuminated in a alternating sequence by blue (460 nm) and green (540 nm) light. Any differences in the intensities of these lights, as perceived by the subject, will result in the subject seeing a flickering light at the aperture 192. The subject can then adjust the position of the wedge 20 until the flickering is eliminated, or is at a minimum. If necessary, further adjustments can be made to the speed of rotation of the shutter 18 further to reduce any perceived flickering.

The subject then presses the first record button, which causes the data processing and printer interface unit 160 to save data on the wedge position obtained from the converter 158. This also causes the motor 22 to move the wedge 20, so as to introduce an offset in wedge position after the position selected by the subject has been recorded. The offset prevents the subject from consciously or subconsciously cheating by renumbering the previous settings of the adjusting knob.

The subject repeats the task of adjusting the wedge for elimination of flicker, pressing the first record button after each adjustment. The subject then fixates on the eccentrically placed light emitting diode and adjusts the wedge again for elimination of flicker. This is repeated several times with the second record button being pressed after each adjustment to log the corresponding wedge positions.

When the subject presses the print switch, the unit 160 automatically calculates the average macular pigment optical density and standard error, and sends the results to the printer 218. After the results have been printed, the unit 160 erases all the same data and starts another processing loop.

We claim:

1. A flicker photometer comprising beam generating means for generating two beams of light, viewing means for enabling a subject to view different coloured light from the beams and adjustment means for adjusting the intensity of light from one beam relative to that of the other beam, wherein the adjustment means comprises an attenuating filter movably mounted in the path of one beam, the filter being so arranged that movement of the filter relative to the beam alters the degree to which the filter attenuates the beam, and an electric motor for moving the filter relative to the beam to achieve said adjustment.

2. A photometer according to claim 1, in which the motor is a stepper motor.

3. A photometer according to claim 2, in which the motor operates in response to pulsed signals derived from control means at least part of which is mounted on the exterior of the photometer to enable the subject to operate the adjustment means.

4. A photometer according to claim 3, in which the control means comprises a dual-phase encoder for generating two sets of pulses, the frequency of which represents the degree of movement of the encoder, and the relative phase of which represents the direction in which the encoder has been moved, and hence the direction in which the filter is to move, wherein the motor is operable to move the filter in the direction determined by the direction of movement of the encoder and over a distance determined by the extent of movement of the encoder.

5. A photometer according to claim 3, in which the control means is arranged selectively to provide coarse or fine control of the movement of the motor, for any given movement of the encoder.

6. A photometer according to claim 4, in which the encoder comprises a rotary knob.

7. A photometer according to claim 4, in which the encoder is an optical encoder.

8. A photometer according to claim 1, in which the filter comprises a graded filter.

9. A photometer according to claim 8, in which the filter comprises a wedge mounted for linear movement relative to the beam such that said movement varies the thickness of the portion of the wedge through which the beam passes, and hence the degree of attenuation of the beam.

10. A photometer according to claim 1, in which the photometer includes screen means for scattering light from the beams before that light enters the viewing means.

11. A photometer according to claim 10, in which the beam generating means, adjustment means and screen means are mounted on a table which is movable relative to the viewing means to enable the photometer to accommodate both near and far-sighted subjects.

12. A photometer according to claim 1, in which the photometer includes measuring means, operable for measuring the position of the filter and generating an output signal representative of that position in response to the operation of a control on the photometer, wherein the operation of the control also causes the motor to move the filter out of the measured position.

13. A photometer according to claim 12, in which the control comprises a button.

14. A flicker photometer comprising beam generating means for generating two beams of light of different wavelengths, viewing means for enabling a subject to view the light from the beams incident on the viewing means, shutter means for causing the incidence of light from one beam on the viewing means rapidly to alternate with that of the other beam, adjustment means for adjusting the intensity of the light from one beam to that of the other beam, wherein the generating means, adjustment means and shutter means are mounted on a table which is movable relative to the viewing means to enable near and far-sighted subjects to use the photometer.

* * * * *